(12) United States Patent
Goldfain et al.

(10) Patent No.: US 6,527,390 B2
(45) Date of Patent: *Mar. 4, 2003

(54) EYE VIEWING DEVICE FOR LARGE FIELD VIEWING

(75) Inventors: Ervin Goldfain, Syracuse, NY (US); William Lagerway, Auburn, NY (US); Chris R. Roberts, Skaneateles, NY (US); Steven R. Slawson, Camillus, NY (US); Allan I. Krauter, Skaneateles, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/033,557

(22) Filed: Dec. 27, 2001

(65) Prior Publication Data

US 2002/0089644 A1 Jul. 11, 2002

Related U.S. Application Data

(63) Continuation of application No. 09/444,161, filed on Nov. 22, 1999, now Pat. No. 6,409,341, which is a continuation-in-part of application No. 09/198,545, filed on Nov. 24, 1998, now Pat. No. 6,065,837.

(51) Int. Cl.[7] .................................................. A61B 3/00
(52) U.S. Cl. ...................... 351/200; 351/205; 351/206; 351/214; 351/215; 351/221; 351/246
(58) Field of Search ................................ 351/205, 206, 351/214, 215, 221, 246

(56) References Cited

U.S. PATENT DOCUMENTS

| | | | | |
|---|---|---|---|---|
| 5,815,242 A | * | 9/1998 | Anderson et al. | 351/221 |
| 6,151,167 A | | 11/2000 | Melville | 359/618 |
| 6,206,522 B1 | * | 3/2001 | Malonet et al. | 351/205 |

OTHER PUBLICATIONS

H. Urey et al., "Optics Designs and System MTF for Laser Scanning Displays", Microvision, Inc.

R. Rutkowski, "Retinal Scanning Displays in Mobile Handsets: Changing the Fugure . . . Right Before Your Eyes", Microvision, Inc.

"Retinal Scanning Displays—How it Works", Microvision, Inc.

H. Urey et al., "Scanner Design and Resolution Tradeoffs for Miniature Scanning Displays", Microvision, Inc.

"Microvision Demonstrates Novel Letter–Scanning Engine for Bar Code Products Company Says Devices Equipped with Low Cost Scanning Technology Will Make Mobile Internet Scanning Possible at 'Giveaway' Prices", Todays News.

* cited by examiner

Primary Examiner—George Manuel
(74) Attorney, Agent, or Firm—George S. Blasiak; Wall Marjama & Bilinski

(57) ABSTRACT

The invention is a low cost, low input power eye viewing device well suited for viewing wide field retinal images through an undilated pupil. Included in the device are a converging light illumination system and an aperture stop. The converging light illumination system provides ease of entry of light rays into an eye, wide field retinal illumination, reduced glare and reduced power consumption. The aperture stop blocks unwanted received glare light not forming part of the retinal image. The device is made especially well suited for retinal viewing through an undilated pupil if the aperture is sized in accordance with the diameter of an undilated pupil.

58 Claims, 8 Drawing Sheets

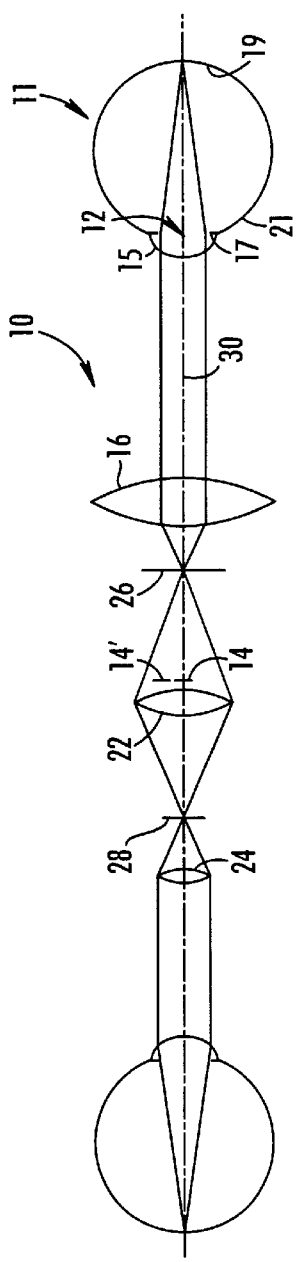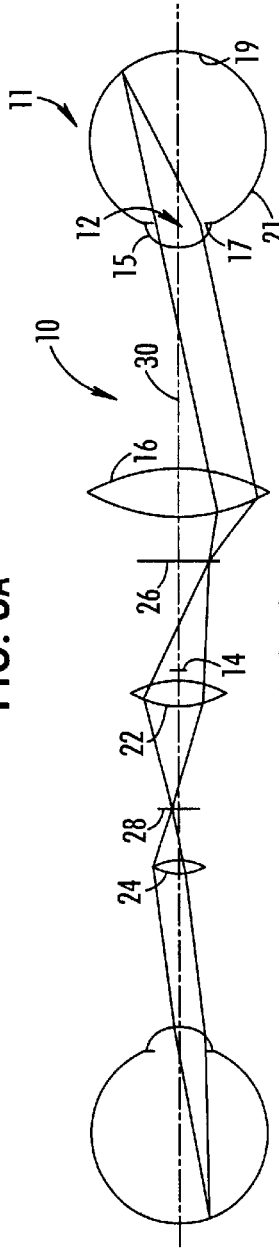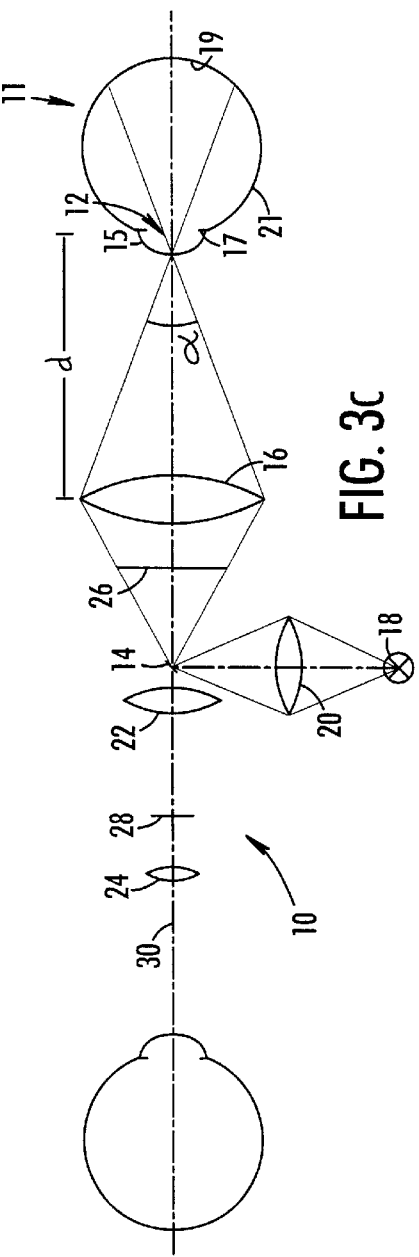
FIG. 3A
FIG. 3B
FIG. 3C

EYE VIEWING DEVICE FOR LARGE FIELD VIEWING

CROSS REFERENCE TO RELATED APPLICATIONS

This application is a continuation application of U.S. Ser. No. 09/444,161, filed Nov. 22, 1999, now U.S. Pat. No. 6,409,341, entitled "Eye Viewing Device for Retinal Viewing Through Undilated Pupil," which is a continuation-in-part of U.S. Ser. No. 09/198,545, filed Nov. 24, 1998, entitled "Ophthalmoscope Comprising Defocused Light Source," now U.S. Pat. No. 6,065,837 issued May 23, 2000. The priorities of both of the above applications are claimed and both of the above applications are incorporated herein by reference.

BACKGROUND TO THE INVENTION

1. Field of the Invention:

This invention relates generally to medical diagnostic instruments, and specifically to an eye viewing device for use in eye viewing.

2. Background of the Prior Art:

Commercially available eye viewing devices for use in retinal viewing have been observed to exhibit numerous limitations.

According to an indirect ophthalmoscope design, a beam splitter is provided in the optical viewing path which directs illumination light rays into an eye, and simultaneously allows receive imaging light rays to pass therethrough. The substantial light losses inherent with this design require that a large, high powered light source be incorporated in the device for the device to satisfactorily illuminate a retina. High powered light sources, in general, are difficult to package, consume excessive amounts of electrical input power, and produce large amounts of heat and unwanted light such as glare. High powered light sources also have large filaments, typically larger than the diameter of an undilated pupil. This makes indirect ophthalmoscopes especially susceptible to glare problems attributable to incident light rays being reflected from outer eye structures such as the iris, cornea and sclera.

Cameras for use in retinal viewing, such as fundus cameras, provide high quality imaging. However, retinal viewing cameras, in general, are expensive, typically require pupil dilation for retinal viewing, and typically require operation by a highly skilled and trained camera operator.

There is a need for a compact, lower input power eye viewing device which provides appropriate retinal illumination and which facilitates wide field retinal viewing without requiring pupil dilation.

SUMMARY OF THE INVENTION

According to its major aspects and broadly stated, the present invention is a low input power, low cost eye viewing device for use in viewing a retina. The device provides wide field retinal viewing without pupil dilation.

In one aspect, an eye viewing device according to the invention includes a converging light illumination system adapted to generate light rays which, when the device is in an operative position, converge at about a pupil of a patient and diverge inside an eye to illuminate a wide retinal field. The converging light illumination system provides illumination of a wide retinal field through a small pupil which may be in an undilated state. The converging light illumination system also reduces electrical input power consumption and reduces glare, as substantially all light delivered by the illumination system enters an eye through a patient's pupil without being reflected from an eye structure outside of a pupil opening such as the iris and sclera.

In another aspect, an eye viewing device of the invention includes a viewing system having an aperture stop positioned substantially conjugate to a patient's pupil and substantially coaxial with an imaging axis of the viewing system. An aperture stop positioned substantially conjugate to a patient's pupil and substantially coaxial with an imaging axis operates to admit light that forms a retinal image and to block light that does not form the retinal image. The aperture stop operates to block unwanted light both when the device is positioned forward of an operative position and when the device is in an operative position. The aperture stop thereby reduces glare and improves image quality both during entry of the device into an eye (when the device is being maneuvered into an operative position) and during retinal viewing (when the device is in an operative position).

The eye viewing device is made especially well suited for retinal viewing through an undilated eye by sizing the aperture of the aperture stop in accordance with the diameter of a pupil of an undilated eye. By sizing the aperture in accordance with the diameter of an undilated pupil, the aperture stop operates to block substantially all light reflected from eye structures outside the diameter of a pupil (such as the iris and sclera).

These and other features of the invention will become clear to those skilled in the art from a careful reading of the Detailed Description of the Preferred Embodiments in connection with the referenced drawings.

BRIEF DESCRIPTION OF THE DRAWINGS

The preferred embodiment of the invention will now be described by way of example only, with reference to the accompanying figures wherein the elements bear like reference numerals, and wherein:

FIG. 3A is a functional schematic diagram of an embodiment of the invention showing light rays from an on-axis object illustrating operation of an embodiment of an imaging system according to the invention having a defocused mirror;

FIG. 3B is a functional schematic diagram of an embodiment of the invention showing light rays from an off-axis object illustrating operation of an imaging system according to the invention having a defocused mirror;

FIG. 3C is a functional schematic diagram of an embodiment of the invention showing illumination light rays which illustrate operation of an illumination system having an on-axis light source;

DETAILED DESCRIPTION OF THE INVENTION

An exemplary embodiment of an eye viewing device according to the invention is described with reference to FIGS. 1A–1E. Eye viewing device 10 includes an illumination system, the operation of which is described mainly with reference to FIG. 1A, and an imaging system, the operation of which is described mainly with reference to FIG. 1B.

The device of FIGS. 1A–1E is especially well suited for use in viewing a retina through an undilated pupil. Small diameter undilated pupils present numerous challenges to viewing retinal images. Small diameter undilated pupils tend to inhibit the transmission of both incident light directed toward a retina and reflected light corresponding to a retinal image. Furthermore, light that is directed into a pupil and that is blocked from entry into a pupil by highly reflective surfaces of outer eye structures such as the iris and sclera tends to be reflected into a viewing system as glare. As will be explained herein below, the device of FIGS. 1A through 1E includes features which operate in combination to overcome the numerous challenges to viewing a retinal image through an undilated pupil. In one aspect, the device of FIGS. 1A through 1E includes the combination of a converging light source illumination system and an aperture stop. The converging light source illumination system operates to direct a substantial amount of light through a small diameter opening while the aperture stop operates to block glare attributable to light rays being reflected from outer eye structures.

Figure 1A:
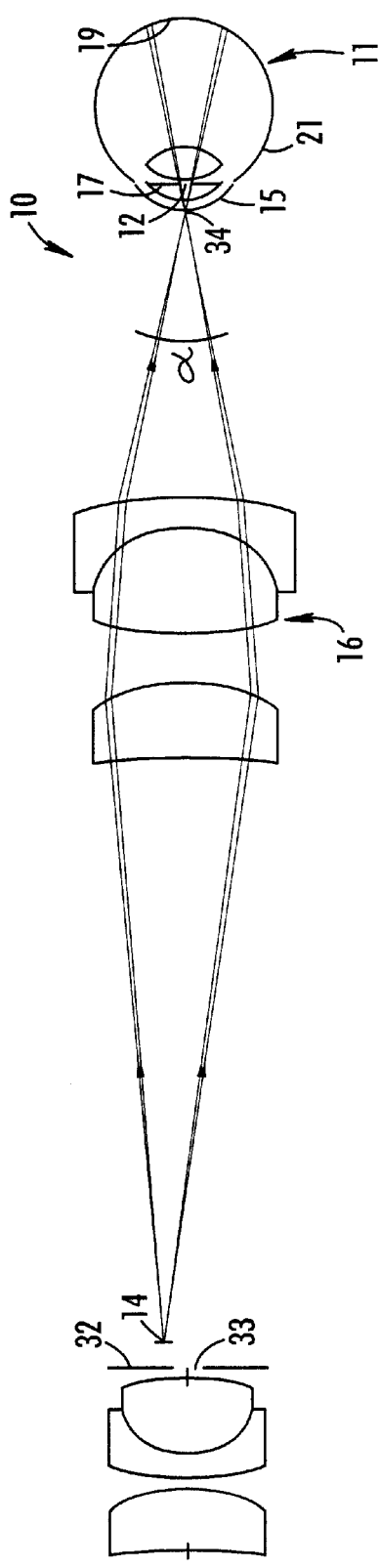
FIG. 1A is a functional schematic diagram of an eye viewing device of the invention showing illumination light rays for illustrating operation of an illumination system according to the invention.

As best seen by FIG. 1A, the illumination system operates to generate illumination light rays which converge at an apex 34 and diverge thereafter. An eye viewing device having a converging light ray illumination system is positioned in an operative position relative to a patient when substantially a maximum amount of incident light enters eye 11 through pupil 12. In the device of FIGS. 1A–1E, an operative position is achieved when apex 34 of the cone of light generated by the illumination system is positioned at about a pupil 12 of a patient. With a converging light ray illumination system, a substantial amount of illumination light enters a small diametered pupil and at the same time illuminates a wide retinal field. A converging light ray illumination system can be provided by the combination of a light source 14 and objective lens 16 positioned forward of the light source 14 for converging light rays emanating from source 14. With a converging light source illumination system, a much higher percentage of incident light rays enter pupil 12 to illuminate retina 19 than are reflected off outer eye structures 17 and 21. Because there is little wasted incident light, a converging light ray illumination system reduces the electrical input power consumption of the illumination system. Because a relatively smaller amount of incident light reflects off outer eye structures such as iris 17 and sclera 21, there is less unwanted light received by the imaging system.

Figure 2:
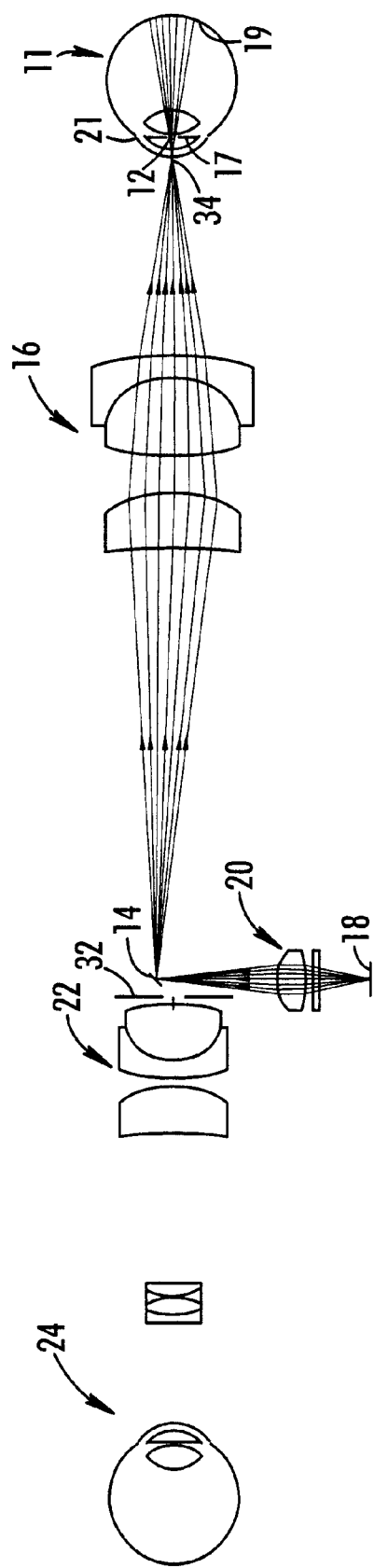
FIG. 2 is a functional schematic diagram showing incident light rays of an illumination system which may be incorporated in the invention.

Light source 14 can be a light generating light source, such as a filament-based lamp, an arc lamp, a fiber optic light source or a solid state light source. However, with presently available technology, light generating light sources are sufficiently large that they introduce packaging problems. Therefore a preferred light source for the eye viewing device is the light source described with reference to FIG. 2. In the embodiment of FIG. 2, light source 14 is provided by a reflective element such as a mirror, which operates in association with a light-generating light source 18, such as a lamp, and a condenser lens 20 which converges light from light source 18 onto mirror 14.

Aspects of the imaging system of the device will now be described with reference mainly to FIG. 1B. The imaging system of the device includes objective-lens 16, imaging lens 22, and an eyepiece lens 24. A retinal image focal plane 26 is produced intermediate objective lens 16 and imaging lens 22, while an eyepiece focal plane 28 is produced intermediate imaging lens 22 and eyepiece lens 24. The imaging system further includes an imaging axis 30 on which lenses 16, 22, and 24 are substantially centered. In all references herein, the term "lens" can refer to a single optical element or a plurality of optical elements functioning together, while an operative position has been defined herein as the position at which substantially a maximum amount of incident light rays enter eye 11 through pupil 12. An operative position can also be defined as the position at which a patient's pupil is conjugate to aperture stop 32.

The retinal image light rays crossing retinal focal plane 26 consist of light rays that enter eye 11 through pupil 12 and which are reflected from retina 19 through pupil 12. Since small undilated pupils tend to inhibit the transmission of both incident light into an eye and reflected retinal image light out of the eye, retinal images viewed through undilated pupils are readily obscured by glare (which is especially prevalent when retinas are viewed through undilated pupils since incident light is more likely to be reflected from highly reflective outer eye structures). In addition to glare attributable to light being reflected from outer eye structures, retinal images can be obscured by glare attributable to other sources such as light that is reflected from a patient's cornea (corneal glare) and light that is reflected from a component of the eye viewing device such as a lens of the device (internal glare).

To the end that the device is well adapted for viewing retinal images through an undilated pupil, device 10 preferably includes features which operate to reduce such glare, and in so doing reduce the percentage of received light rays not corresponding to a retinal image relative to the percentage of received light rays corresponding to a retinal image.

One feature which operates to reduce the percentage of light rays not corresponding to the retinal image is the feature of converging light illumination, described above. In a converging light illumination system, a relatively high percentage of light enters eye 11 through pupil 12, and a relatively low percentage of light is reflected from outer eye structures 17 and 21 as seen in FIG. 1A. Other features which may be incorporated to increase the percentage of retinal image forming received light relative to unwanted light are described hereinbelow.

Figure 1B:
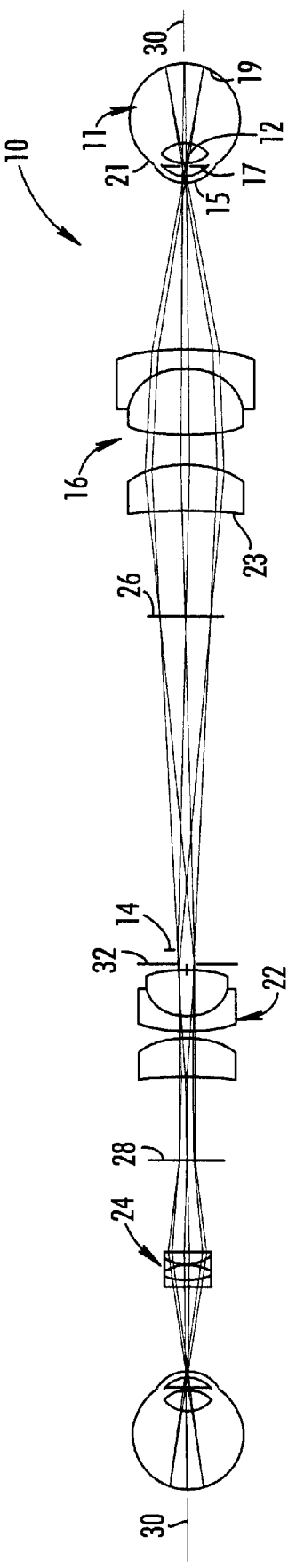
FIG. 1B is a functional schematic diagram of an eye viewing device of the invention showing receive optical light rays which illustrate operation of the devices' imaging system.

In the device of FIG. 1B, an aperture stop 32 is positioned forward of imaging lens 22 to block unwanted light. Aperture stop 32 should be positioned substantially coaxially with imaging axis 30 and substantially conjugate to a patient's pupil 12 when in an operative position in relation to device 10. Positioning of aperture stop 32 substantially coaxial with imaging axis 30 encourages substantially a maximum amount of useful receive imaging light to be admitted through imaging lens 22 without also admitting glare light that originates radially outside the patient's pupil 12. By positioning aperture stop 32 so that it is substantially conjugate to a pupil, aperture stop 32 operates to block light reflected from outer eye structures 17 and 21. Because the apex 34 of the cone of light generated by illumination system is substantially conjugate to a patient's pupil for positioning the device in an operative position, and because the preferred position of aperture stop is also one that is conjugate to the pupil, then the preferred position of aperture stop 32 in a device made in accordance with FIGS. 1A–1E can be described as one that is substantially conjugate to the apex of the cone of light generated by the illumination system.

For optimal blocking of unwanted received light, aperture 33 of aperture stop 32 should be sized in accordance with the diameter of the pupil through which a retina is viewed. The diameter of an undilated pupil is about 2 mm. Accordingly, for optimally configuring device 10 for viewing a retina through an undilated pupil, aperture 33 should be sized to correspond to a patient pupil diameter of about 2 mm. The resulting diameter of aperture 33 is determined by multiplying the pupil diameter by the magnification of the pupil in the plane of the aperture stop 32. This same principle can be applied to optimize the instrument design for other pupil sizes, larger and smaller.

Figure 1C:
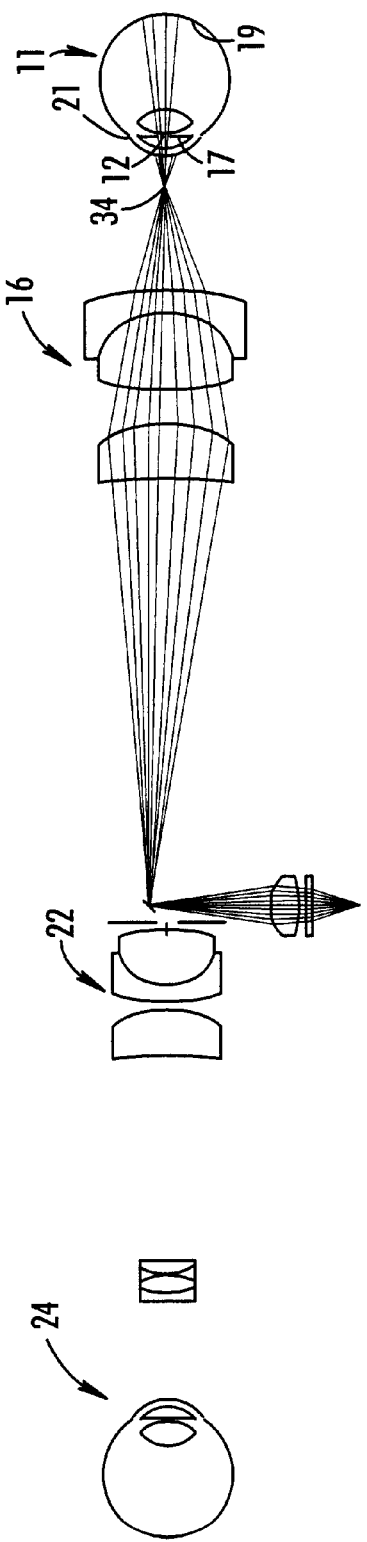
FIG. 1C is a functional schematic diagram of an eye viewing device of the invention showing incident illumination light rays when the device is at a distance away from an operative position.
Figure 1D:
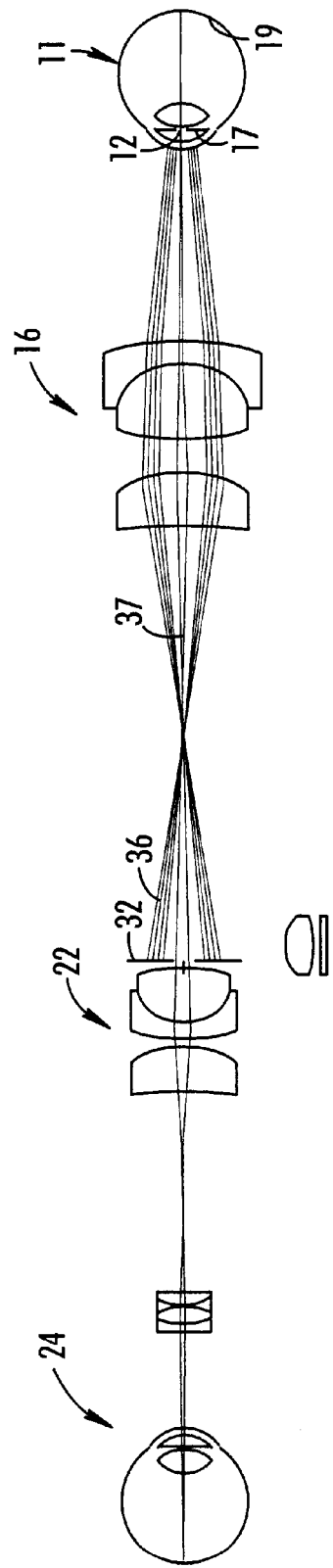
FIG. 1D is a functional schematic diagram of the eye viewing device of FIG. 1C showing receive optical light rays when the device is at a distance away from an operative position.

In addition to reducing glare and improving image quality when device 10 is in an operative position, aperture stop 32 reduces glare and improves image quality prior to the device being moved into an operative position. FIGS. 1C and 1D illustrate illumination light rays exiting the device and reflecting off the eye as they are received in a viewing system of device 10 during entry of the device into an eye (during the process of moving the device into an operative position). FIG. 1C illustrates incident light rays generated by device 10 when the device is at a distance away from an operative position, while FIG. 1D illustrates received reflected light rays of a device positioned at the same distance away from an operative position as is shown in FIG. 1C. It is seen that when the device is away from an operative position, then light rays generated by the illumination system strike eye 11 in a diverged state (apex 34 of the cone of light is positioned forward of pupil 12). Thus, a relatively small percentage of incident rays enter an eye through pupil 12 and a relatively high percentage light rays are reflected from the highly reflective outer surfaces of eye structures such as iris 17 and sclera 21. Light rays reflected from outer eye structures 17 and 21 tend to be reflected at an angle with respect to imaging axis 30. The curved surface of eye 11 assures that reflected light rays are reflected at an angle with respect to axis 30. When device 10 is a substantial distance away from an operative position many light rays reflected from eye 11 during entry of the device are reflected out of the viewing system entirely as is indicated by rays 36'. The majority of light rays that are received in the viewing system are blocked by aperture stop 32 as is indicated by rays 36. Only a small percentage of light rays such as rays 37 pass through aperture 33. Light rays that pass through aperture 33 consist of rays that originated as incident light rays directed substantially along axis 30 and that passed through pupil 12 to retina 19. Thus, during entry of device 10 into eye 11, it can be seen that aperture stop 32 tends to block unwanted light and to pass light corresponding to a retinal image.

It will be seen that without aperture stop 32, a substantial majority of light rays transmitted to eyepiece focal plane 28 during entry would be light rays reflected from outer eye structures 17 and 21. Thus, the image received at eyepiece focal plane 28 would be heavily obscured by glare. With aperture stop 32 the substantial majority of light rays received at eyepiece focal plane correspond to retina 19. During entry into the eye, the user will see a small field image of the retina, known as the "red reflex" which helps an operator move the device into an operative position without significant glare. By maintaining the retinal image spot near the center of eyepiece focal plane 28 and moving the device toward an eye 11, an operative position can easily be achieved.

Additional glare or unwanted light reducing features may be incorporated in the device. As is shown in FIGS. 1A–1E, light source 14 may be positioned just forward of aperture stop 32 outside of the boundary between received and blocked light and off-axis with respect to imaging axis 30 of device 10. Positioning light source forward of aperture stop 32, outside of the boundary between received and blocked light defined by aperture 33, assures that light source 14 has no obscuring effect on the viewed image and assures maximum image brightness in the user's eye. Positioning light source 14 off-axis also reduces both internal and corneal glare. By positioning light source off-axis, incident light that is reflected off of lens 16 or off of cornea 15 is directed at an angle with respect to axis 30 and, therefore, away from the optical receive path.

Figure 1E:
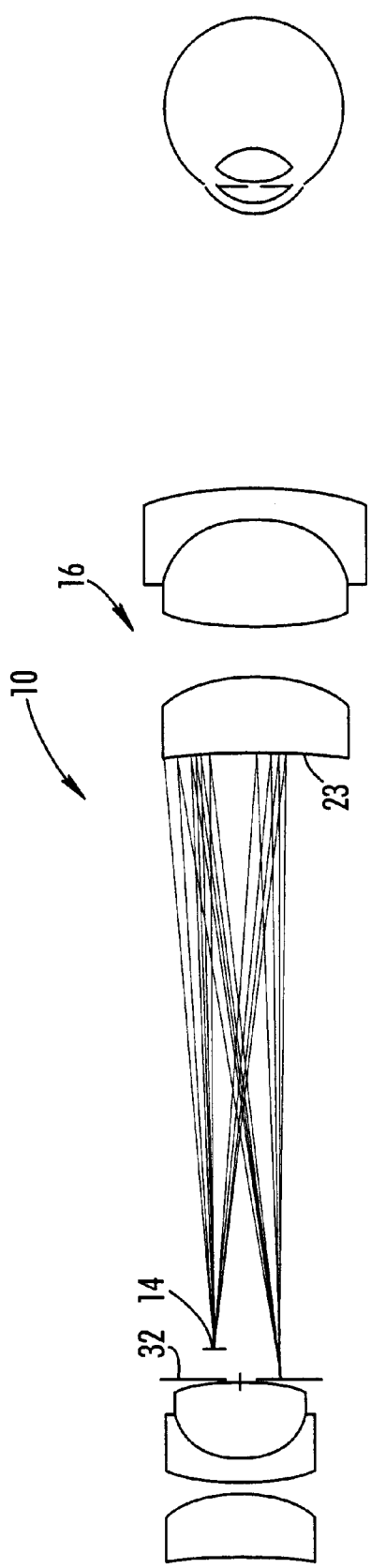
FIG. 1E is a functional diagram of an eye viewing device of the invention showing incident light rays reflected from an objective lens.

Glare may be further reduced by shaping the first surface 23 of objective lens 16 so that first surface 23 is curved and substantially concentric with the center of aperture 33 as seen by the embodiment of FIG. 1E. This assures that light that is reflected from surface 23 is reflected to a point equal to and opposite light source 14 with respect to imaging axis 30. If light source 14 is positioned outside of the boundary dividing blocked and received light defined by aperture 33, the concentric curved first surface 23 assures that internal glare resulting from light being reflected from surface 23 is blocked by aperture stop 32.

In addition to the above features reducing unwanted received light, glare can be reduced by disposing linear polarizers in the imaging and illumination paths in a crossed configuration.

An alternative embodiment of the invention is described with reference to FIGS. 3A–3C. In the embodiment shown in FIGS. 3A–3C, light source 14 is disposed directly in the field of view in a highly defocused position in relation to focal planes 26 and 28. By disposing light source 14 on imaging axis 30, light source 14 provides for maximally efficient illumination of a retina 19. Positioning the light source off-axis as is shown by light source 14' results in less-than-maximally efficient retinal illumination, but also reduces glare for reasons that have been discussed herein.

Light source 14 in the embodiment of FIGS. 3A–3C should be positioned in a highly defocused position in relation to any image plane of the eye viewing device conjugate to a patient's retina 19 in an operative position in relation to device 10. As shown in the imaging system diagrams of FIGS. 3A–3C, a highly defocused position for source 14 in relation to an image focal plane conjugate to a retina is provided by disposing source 14 intermediate retinal focal plane 26 and imaging lens 22. In general, source 14 becomes less in focus at any plane conjugate to and including eyepiece focal plane 28 as the source is moved toward imaging lens 22 and away from retinal focal plane 26. Preferably, source 14 is positioned as close as is physically possible to lens 22.

Corneal glare can be reduced in the embodiment of FIGS. 3A–3C if source 14 is disposed in device 10 in a position that is conjugate to the surface of a cornea when the device is in an operative position in relation to a patient. If light source 14 is positioned conjugate to cornea 15, many light rays which do happen to be reflected from cornea 15 are imaged directly onto light source 14. If light source 14 is provided by a reflective element as shown, these light rays correspond to a cornea image and are blocked before reaching eyepiece focal plane 28, thereby reducing corneal glare.

In a specific example of an eye viewing device designed according to the general configuration described with reference to FIGS. 1A–1E and 3A–3C, the objective lens 16 may be provided by a lens system having a focal length of about 25 mm, and a back focal length of about one-half the focal length. The eye viewing device may be configured so that the lens surface closest to the-patient in the objective lens system is positioned about 25 mm from a patient's cornea when in an operative position. The objective lens system accepts parallel or nearly parallel light from a patient's eye and focuses the light to an internal image located at or near the back focal plane 26 of the objective. The objective lens system may have a diameter of about 25 mm. Imaging lens 22, meanwhile, may be provided by a lens system having a focal length of about 25 mm, a back focal length of about 18 mm and a clear aperture of about 20 mm. The imaging lens may project an internal image from the objective focal plane 26 to eyepiece focal plane 28 at a magnification of about 0.6X. Eyepiece focal plane 28 may have an aperture of about 8 mm in diameter, corresponding to the focal plane diameter of a typical 20X eyepiece. The axial length from objective lens 16 to eyepiece focal plane 28 may be about 160 mm. In the illumination system described with reference to FIG. 3C, condenser lens 20 may be provided by a condenser system having a numerical aperture of about 0.2 to 0.4, working at a magnification of about 1X to 2X, with a focal length of about 9 mm. In the embodiment of FIGS. 1A–1E, aperture stop 32 may be positioned substantially normal to axis 30 and approximately halfway between the most rearward point of light source 14 and the most forward point of imaging lens 22. Aperture stop 32 may have an aperture diameter of about 4.6 mm.

Figure 4:
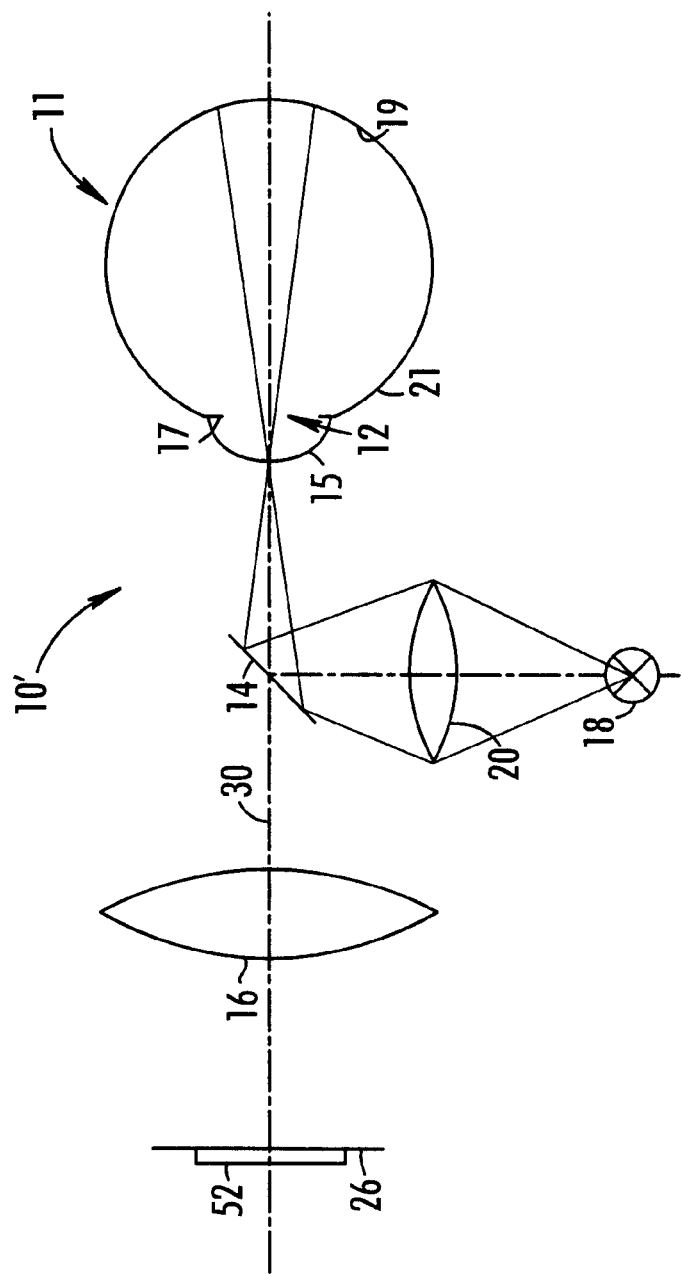
FIG. 4 is a functional schematic diagram of another embodiment of the invention having a defocused light source.

An alternative optical configuration for the eye viewing device of FIGS. 3A–3C having a defocused light source is described with reference to FIG. 4. In the eye viewing device of FIG. 4, light source 14 is disposed forward of objective lens 16 and imaging lens 22 is deleted. Light source 14 is disposed in a highly defocused position in relation to retinal focal plane 26 by disposing light source 14 in proximity with objective lens 16. In the embodiment of FIG. 4, objective lens 16 does not form part of the optical illumination system. Instead, illumination light rays which converge at a cornea 15 and diverge toward a retina 19 are formed by disposing condenser lens 20 in relationship with light source mirror 14 such that light rays reflected from the mirror converge after being reflected. Further with reference to the embodiment of FIG. 4, eyepiece lens 24 may optionally be removed and replaced with image-sensor 52, such as a CCD image sensor, which is positioned on retinal focal plane 26. A processor system (not shown) in communication with sensor 52, can be configured to capture image signals generated by sensor 52, process such signals, and if desirable, electronically reverse or magnify any captured images to accomplish the function provided optically by imaging lens 22 of the eye viewing device of FIGS. 1A–3C.

The conventional lenses in the systems described hereinabove can be replaced with similarly functioning optical elements such as diffractive lenses, binary gratings, phase filters, holographic optical elements (HOE), gradient-index lenses, and hybrid optical elements.

Figure 5:
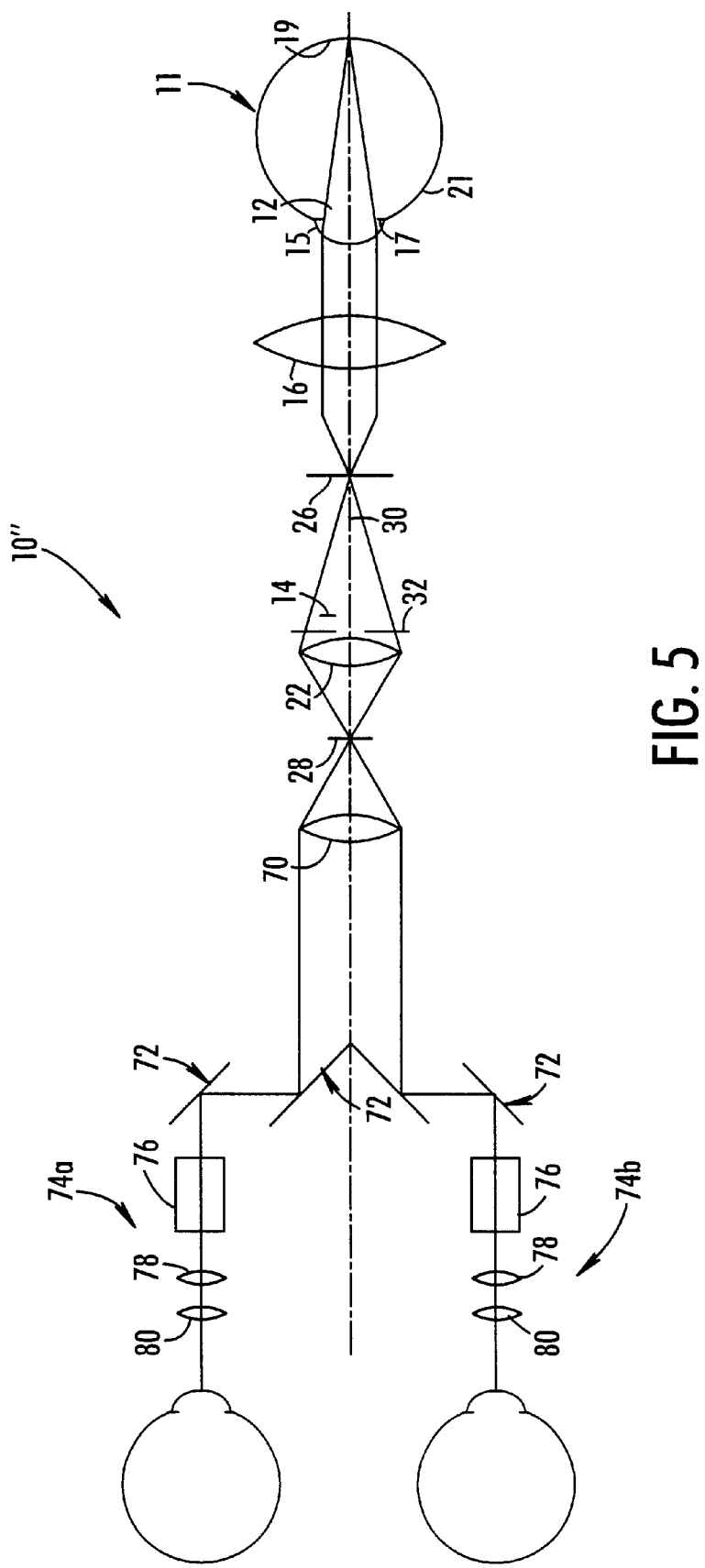
FIG. 5 is functional schematic diagram of the invention configured for binocular viewing.

The invention can be adapted to provide binocular viewing as is illustrated by the embodiments of FIG. 5. As seen in FIG. 5, a binocular eye viewing device according to the invention typically includes a collimating optical element 70 for collimating light rays of the imaging path, and separating optics 72 for splitting light rays transmitted by collimating optics 70 into two separate imaging paths 74A and 74B. Separating optics 72 typically include a combination of such optical elements as prisms and/or mirrors. Continuing with reference to FIG. 5, binocular eye viewing device 10" may further include orientation optics 76 disposed in each binocular imaging path 74A, 74B for setting the orientation of images transmitted by separating optics as is necessary. Orientation optics 76 may include such optical elements as prism and/or mirror optical elements. Binocular eye viewing device 10" may further include decollimation optics 78 and eyepiece optics 80 disposed in each imaging path 74A and 74B. Each eyepiece optics 80 collimates light so that images can be perceived by a viewer. The eye tubes (not shown) of eyepiece optics 80 may be arranged in an orientation slightly diverging toward a viewer's eyes to approximate the direct viewing condition of a target by a pair of eyes.

Several functional aspects of the invention have been described. Certain additional features which may be incorporated in physical embodiments of the invention will now be described in detail.

Figure 6:
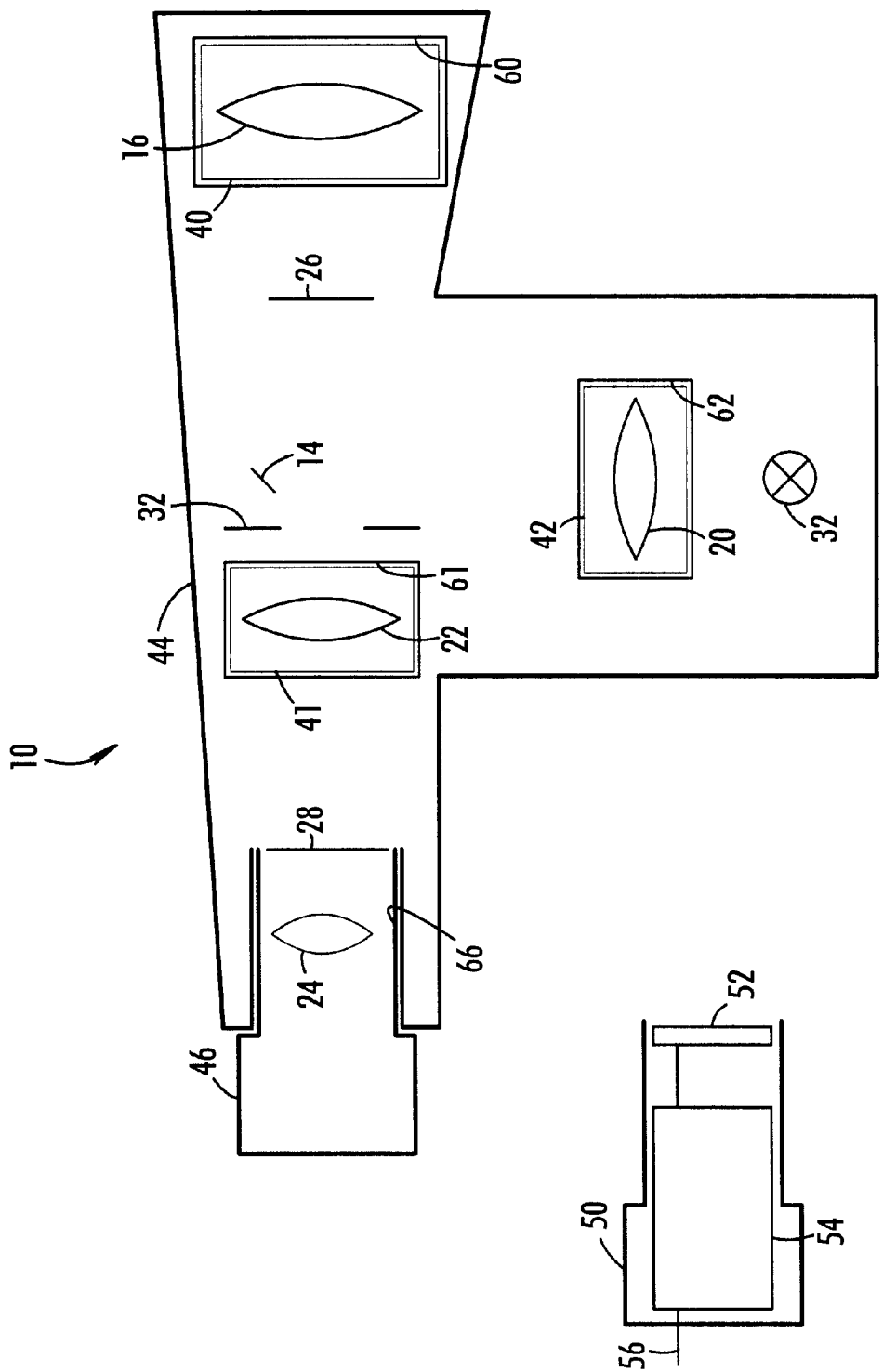
FIG. 6 is a physical schematic diagram illustrating various features which may be incorporated in a physical embodiment of the invention.

Shown in FIG. 6 is a physical schematic diagram of an embodiment of the invention which can be reconfigured for optimizing various functional aspects of the eye viewing device. In the embodiment of FIG. 6, housing 44 of eye viewing device 10 includes lens holders 60, 61, 62 and 66 and replaceable lens modules 40, 41, 42 and 46 replaceably received in their respective holders. As will be explained hereinbelow, replacing a certain lens module or a grouping of lens modules changes functional aspects of the eye viewing device enabling the ophthalmoscope to be optimized for a specific intended use.

For example, with reference to FIGS. 1A–1E, and 3A–3C, it is seen that the area of retina 19 that is illuminated by the illumination system depends on the diameter and optical power of objective lens 16 and on the magnification selected for the lens at the operative position of the eye viewing device. This area corresponds to the angle a as shown in FIGS. 1A and 3C. The field of view of the imaging system, meanwhile, also depends on the diameter and optical power of objective lens 16 and on the magnification of the lens at the operative position of the eye viewing device.

It is desirable that eye viewing device 10 images a wide field of view. While a wide field of view and illumination angle, α, are highly desirable for an accurate and efficient diagnosis of various problems, a smaller field of view and illumination angle are desirable for ease of use. As the angle of illumination, α, becomes less steep, illumination light rays are more easily directed into an eye through a pupil, so that entry into an eye is easier. This is because as the illumination angle, α, becomes less steep, light rays from source 14 can be directed through pupil 12 over a greater range of cornea-to-lens distances. Accordingly, in view of the above, it would be beneficial to provide an eye viewing device which could be configured either for optimized field of view or optimized ease of use.

In a preferred embodiment, the imaging system of device 10 images a field that contains the area of a retina that is illuminated by the illumination system. Most preferably the area of the retina that is imaged by the imaging system is about 15 percent to 30 percent larger than the area that is illuminated. This feature provides improved orientation of a viewed field and reduces alignment considerations between illumination and viewing.

A possible embodiment of reconfigurable eye viewing device according to the invention is described with reference to the physical schematic diagram of FIG. 6. This particular physical layout diagram includes first and second lens modules 40 and 41. First lens module 40 includes objective lens 16, while second lens module 41 includes imaging lens 22. While the field of view and illumination angle depend mainly on the sizing, optical power, and magnification selected for objective lens 16, imaging lens 22 will normally be replaced along with lens 16, since the sizing and optical power of lens 16 are coordinated with those of lens 22. The housing 44 and lens modules 40, 41 are complementarily designed so that the modular lens modules can be manually removed and replaced from housing 44 while maintaining a common eyepiece focal plane 28. In a reconfigurable eye viewing device, a first set of lens modules can be provided to configure the eye viewing device for imaging a wide field of view, while a second set of modules can provide a reduced field of view (but with increased magnification), making the instrument easier to maneuver into an operative position. Such a device can be made easier to use simply by replacing the first set of lens modules with the second set of lens modules.

To complement the change in field of view accomplished by changing the first and second lens modules, the illumination condenser system may also be changed in a modular fashion to optimize the illumination characteristics to suit the user's needs. In all condenser systems with a given condenser size, the ability to collect the light from a light generating light source is balanced with the angle at which the light can be transmitted and the magnification at which the image of the light generating light source is projected. The lenses inside the illumination lens module 42 can be selected such that the illumination system matches the illumination numerical aperture of the given objective module 40.

In a further alternate embodiment, the invention can be adapted to capture electronic images representing an imaged retina one such embodiment is described with reference to FIG. 6. In FIG. 6, an eye viewing device 10 is shown that can be reconfigured for electronic image capture. FIG. 6 shows an eye viewing device adapted so that eyepiece module 46 can be replaced with a video module 50. It is seen that eye viewing device 10 normally includes an eyepiece module 46 having an eyepiece lens 24 which collimates imaging light rays so that a retinal image can be viewed by a user. Eyepiece 46 can be replaced with video module 50 which includes certain components that configure the eye viewing device for video capture. In particular, a video module 50 may contain an image sensor 52, such as a CCD image sensor, which is in an operative position in relation to the imaging system when the video module is installed in holder 66. The image sensor 52 is in electrical communication with a processor system 54 which may be programmed to control image sensor 52 and to capture and, possibly to store image data generated by and received from image sensor 52. While processor system 54 is shown as being disposed in video module 50, it is understood that processor system 54 could be disposed external to video module 50. The video module 50 may further be in communication with an external display screen and/or an external processing system via cable 56, for example, so that video images captured by image sensor can be displayed or otherwise output, and possibly archived.

Video module 50 can be designed so that image sensor 52 lies on eyepiece focal plane 28 when module 50 is in an operative position in holder 66. It is seen that an eye viewing device of the invention can be configured for video capture by replacing eyepiece module 46 with a video module 50 without adding or replacing additional lenses of the imaging system. Alternative sized imagers may also be used, with the addition of image resizing lenses. Such a configuration shifts the location of focal plane 28.

While the present invention has been particularly shown and described with reference to the preferred mode as illustrated in the drawings, it will be understood by one skilled in the art that various changes in detail may be effected therein without departing from the spirit and scope of the invention as defined by the claims.

What is claimed is:

1. An eye viewing device for viewing a structure of an eye having a pupil, said device comprising:

an illumination system generating a converging cone of light that converges at an apex and diverges thereafter;

an imaging system having an imaging axis; and an aperture stop disposed in said device substantially coaxial with said imaging axis and substantially conjugate to said apex whereby corneal glare is reduced.

2. The eye viewing device of claim 1, wherein an aperture of said aperture stop is sized to substantially correspond to a size of said pupil.

3. The eye viewing device of claim 1 wherein an aperture of said aperture stop is sized substantially according to the formula, d=2 m millimeters, where d is a diameter of the aperture and m is the magnification of said pupil in a plane of said aperture stop.

4. The eye viewing device of claim 1, further comprising a housing, wherein said illumination system includes a light source positioned off-axis with respect to said imaging axis, whereby internal and corneal glare in said device is reduced.

5. The eye viewing device of claim 4, wherein said off-axis positioned light source is a light generating light source.

6. The eye viewing device of claim 4, wherein said off-axis positioned light source is provided by a light reflective element.

7. The eye viewing device of claim 4, wherein said off-axis positioned light source is provided by a mirror.

8. The eye viewing device of claim 1, wherein said device includes a first end adapted for positioning toward said pupil and wherein said illumination system includes a light source positioned toward said first end of said device relative to said aperture stop.

9. The eye viewing device of claim 1, wherein said imaging system includes an objective lens and said illumination system includes a light source, said objective lens having a first surface closest to said light source curved substantially concentric about a center of an aperture of said aperture stop, whereby internal glare in said device is reduced.

10. The eye viewing device of claim 1, wherein said illumination system includes a light source positioned outside of a border between received and blocked light defined by an aperture stop, whereby said light source has no obscuring effect on images received by said viewing device.

11. The eye viewing device of claim 1, wherein said illumination system includes a light source positioned outside of a border between received and blocked light defined by said aperture stop and wherein said imaging system includes an objective lens having a curved first surface curved concentric about a center of said aperture, whereby said light source has no obscuring effect on images received by said viewing device, and whereby incident light reflected from said first surface is blocked by said aperture stop.

12. The eye viewing device of claim 1, wherein said imaging system comprises binocular optics adapted to provide binocular viewing.

13. The eye viewing device of claim 1, wherein said device includes a housing including at least one lens holder, and a plurality of lenses, at least one of said lenses being packaged in a lens module which is adapted to be received in said at least one lens holder.

14. The eye viewing device of claim 1, wherein a retinal field of view of said imaging system is larger than a retinal area of illumination of said illumination system.

15. The eye viewing device of claim 1, wherein a retinal field of view of said imaging system is between about 15 to 30 percent larger than a retinal area of illumination of said illumination system.

16. The eye viewing device of claim 1, wherein said aperture stop is disposed in said device so that said aperture stop is substantially conjugate to said pupil when said illumination system projects substantially a maximum amount of light through said pupil.

17. The eye viewing device of claim 1, wherein said imaging system includes an objective lens disposed in a path of illumination light rays generated by said illumination system.

18. The eye viewing device of claim 1, wherein said illumination system includes an objective lens disposed so that said imaging axis intersects said objective lens.

19. An eye viewing device for viewing a structure of an eye having a retina and a pupil, said device comprising:
   an illumination system for illuminating said retina;
   an imaging system having an imaging axis; and
   an aperture stop disposed in said device substantially coaxial with said imaging axis and substantially conjugate to said pupil when said device is in an operative position in relation to said eye, whereby corneal glare is reduced.

20. The eye viewing device of claim 19, wherein an aperture of said aperture stop is sized to substantially correspond to a size of said pupil.

21. The eye viewing device of claim 19, wherein an aperture of said aperture stop is sized substantially according to the formula, d=2 m millimeters, where d is a diameter of said aperture and m is the magnification of said pupil in a plane of said aperture stop.

22. The eye viewing device of claim 19, further comprising a housing wherein said illumination system includes a light source positioned off-axis with respect to said imaging axis, whereby internal and corneal glare in said device is reduced.

23. The eye viewing device of claim 19, wherein said off-axis positioned light source is a light generating light source.

24. The eye viewing device of claim 19, wherein said off-axis positioned light source is provided by a light reflective element.

25. The eye viewing device of claim 19, wherein said off-axis positioned light source is provided by a mirror.

26. The eye viewing device of claim 19, wherein said device includes a first end adapted for positioning toward said pupil and wherein said illumination system includes a light source positioned toward said first end of said device relative to said aperture stop.

27. The eye viewing device of claim 19, wherein said imaging system includes an objective lens, said objective lens having a first surface closest to said light source curved substantially concentric about a center of an aperture of said aperture stop, whereby internal glare in said device is reduced.

28. The eye viewing device of claim 19, wherein said illumination system includes a light source positioned outside of a border between received and blocked light defined by an aperture stop, whereby said light source has no obscuring effect on images received by said viewing device.

29. The eye viewing device of claim 19, wherein said illumination system includes a light source positioned outside of a border between received and blocked light defined by said aperture stop and wherein said imaging system includes an objective lens having a curved first surface curved concentric about a center of said aperture, whereby said light source has no obscuring effect on images received by said viewing device, and whereby incident light reflected from said first surface is blocked by said aperture stop.

30. The eye viewing device of claim 19, wherein said imaging system comprises binocular optics adapted to provide binocular viewing.

31. The eye viewing device of claim 19, wherein said device includes a housing including at least one lens holder, and a plurality of lenses, at least one of said lenses being packaged in a lens module which is adapted to be received in said at least one lens holder.

32. The eye viewing device of claim 19, wherein a retinal field of view of said imaging system is larger than a retinal area of illumination of said illumination system.

33. The eye viewing device of claim 19, wherein a retinal field of view of said imaging system is between about 15 to 30 percent larger than a retinal area of illumination of said illumination system.

34. The eye viewing device of claim 19, wherein said illumination system generates converging light converging at an apex, wherein said aperture stop is disposed in said device in a position substantially conjugate to said apex.

35. The eye viewing device of claim 19, wherein said imaging system includes an objective lens disposed in a path of illumination light rays generated by said illumination system.

36. The eye viewing device of claim 19, wherein said illumination system includes an objective lens disposed so that said imaging axis intersects said objective lens.

37. An eye viewing device having a patient end and an observer end, said device comprising:
   a compact housing;
   an illumination system including a light source generating illumination light rays for illuminating a structure of an eye;
   an imaging system including an imaging axis and an objective lens; and
   an aperture stop disposed about said imaging axis,
wherein said device is configured so that said illumination light rays pass through said objective lens, wherein said light source, said objective lens, and said aperture stop are incorporated in said housing.

38. The eye viewing device of claim 37, wherein said aperture stop is disposed coaxially relative to said imaging axis.

39. The eye viewing device of claim 37, wherein said aperture stop is sized to substantially correspond to a size of a pupil.

40. The eye viewing device of claim 37, wherein said illumination system generates converging light converging in an apex, and wherein said aperture stop is disposed substantially conjugate to said apex.

41. The eye viewing device of claim 37, wherein said imaging axis is unfolded.

42. The eye viewing device of claim 37, wherein said illumination system generates converging light converging in an apex, and wherein said aperture stop is disposed in said compact housing so that said aperture stop is in a position that is substantially conjugate to a pupil of said eye when said illumination system projects substantially a maximum amount of light through a pupil of said eye.

43. The eye viewing device of claim 37, wherein said device comprises optics disposed in said compact housing for developing a noninverted image of an eye structure.

44. An eye viewing device having a patient end and an observer end, said device comprising:
   a illumination system generating converging illumination light rays for illuminating a structure of an eye, said illumination light rays converging at an apex;
   an imaging system including an imaging axis and an objective lens; and
   an aperture stop disposed about said imaging axis in a position substantially conjugate to said apex, wherein said device is configured so that said illumination light rays pass through said objective lens.

45. The eye viewing device of claim 44, wherein said aperture stop is disposed substantially coaxially relative to said imaging axis.

46. The eye viewing device of claim 44, wherein said aperture stop is sized to substantially correspond to a size of a pupil.

47. The eye viewing device of claim 44, wherein said aperture stop is disposed in a position so that said aperture stop is in a position that is substantially conjugate to a pupil of said eye when said illumination system projects substantially a maximum amount of light through a pupil of said eye.

48. The eye viewing device of claim 44, wherein said imaging axis is unfolded.

49. An eye viewing device comprising:
   an imaging axis;
   an aperture stop disposed about said imaging axis; and
   an illumination system devoid of a beam-splitter generating converging light rays converging at an apex,
   wherein said illumination system includes an objective lens for converging illumination light rays, and wherein said aperture stop is disposed substantially conjugate to said apex.

50. The eye viewing device of claim 49, wherein said aperture stop is disposed substantially coaxial relative to said imaging axis.

51. The eye viewing device of claim 49, wherein said objective lens is disposed in said device so that said imaging axis intersects said objective lens.

52. The eye viewing device of claim 49, wherein said imaging axis is unfolded

53. The eye viewing device of claim 49, wherein said aperture stop is disposed in a position so that said aperture stop is in a position that is substantially conjugate to a pupil of said eye when said illumination system projects substantially a maximum amount of light through a pupil of said eye.

54. A retinal view ophthalmoscope for viewing a retina of an eye having a pupil, said retinal viewing ophthalmoscope comprising:
   a compact housing having a first section defining a first end of said ophthalmoscope for positioning in proximity with a patient eye and a second end for positioning in proximity with an observer eye;
   an imaging system having an imaging axis, an objective lens, and an aperture stop disposed about said imaging axis, said imaging axis intersecting, both of said first and said second ends of said ophthalmoscope;
   an illumination system devoid of a beam splitter generating light that converges at an apex; and
   an aperture stop disposed conjugate to said apex.

55. The ophthalmoscope of claim 54, wherein said aperture stop is disposed substantially coaxial relative to said imaging axis.

56. The ophthalmoscope of claim 54, wherein said objective lens is disposed in said device so that said imaging axis intersects said objective lens.

57. The ophthalmoscope of claim 54, wherein said imaging axis is unfolded.

58. The ophthalmoscope of claim 54, wherein said aperture stop is disposed in a position so that said aperture stop is in a position that is substantially conjugate to said apex whereby corneal glare is reduced.

* * * * *